United States Patent [19]

Petersen et al.

[11] 4,095,583

[45] Jun. 20, 1978

[54] SELF-CONTAINED WARMING PAD

[75] Inventors: Russell H. Petersen, Sturtevant; Edmund A. Weaver, Racine, both of Wis.; Frederick P. Kober, Bayside, N.Y.

[73] Assignee: Chem-E-Watt Corporation, Racine, Wis.

[21] Appl. No.: 743,437

[22] Filed: Nov. 19, 1976

[51] Int. Cl.² ............................................. F24J 1/04
[52] U.S. Cl. ................................... 126/263; 44/3 A; 132/36.2 B
[58] Field of Search ................. 126/263, 204; 44/3 R, 44/3 A, 3 C; 132/36.2 B; 136/86 A; 128/254, 403

[56] References Cited

U.S. PATENT DOCUMENTS

| | | | |
|---|---|---|---|
| 2,541,736 | 2/1951 | Alexander | 126/263 |
| 3,207,149 | 9/1965 | Spindler | 126/263 |
| 3,774,589 | 11/1973 | Kober | 44/3 A X |
| 3,924,603 | 12/1975 | Chapin | 126/263 |
| 3,980,070 | 9/1976 | Krupa | 126/263 |

Primary Examiner—Edward G. Favors

[57] ABSTRACT

A self-contained warming pad characterized by a heating element, an adjacent dose of activating liquid within a frangible container, and a substantially liquid-impervious cover enclosing the element and frangible container and having at least one tortuous air passage therethrough. Features include a cover having thermal insulating qualities, and a frangible container made of a meltable substance having a melting point chosen to control the upper temperatures of the pad. Other features relate to a cover configuration which provides an annular breathing passage, and a porous resilient mass within the pad which provides a substantial breathing capacity. The heating element is preferably an electrochemical element, and most preferably a complex electrochemical element having two cathode layers and one anode layer in a sandwich-like structure.

41 Claims, 7 Drawing Figures

U.S. Patent  June 20, 1978  Sheet 1 of 2  4,095,583
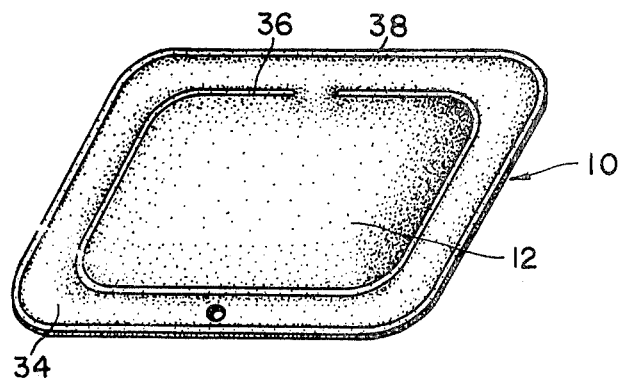
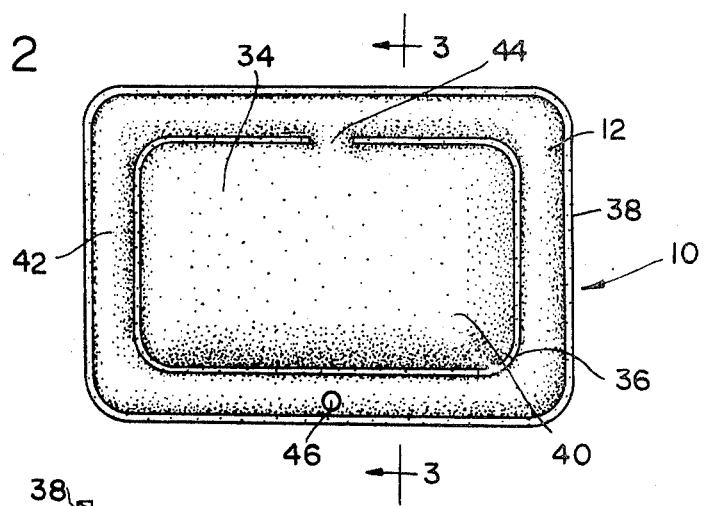
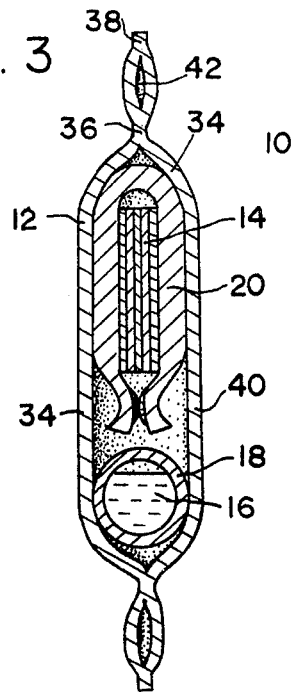
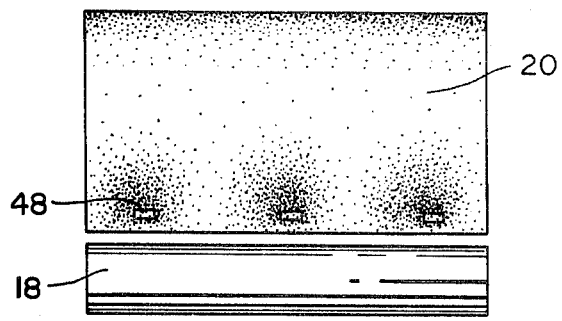

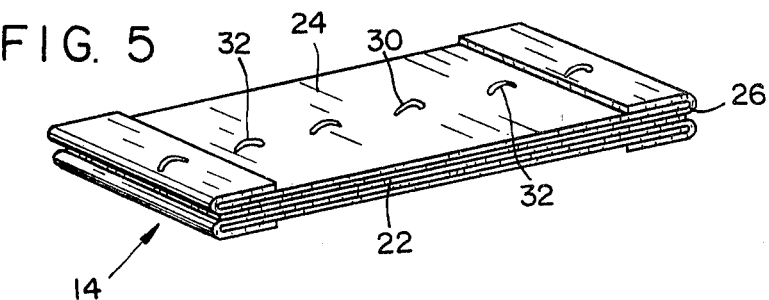
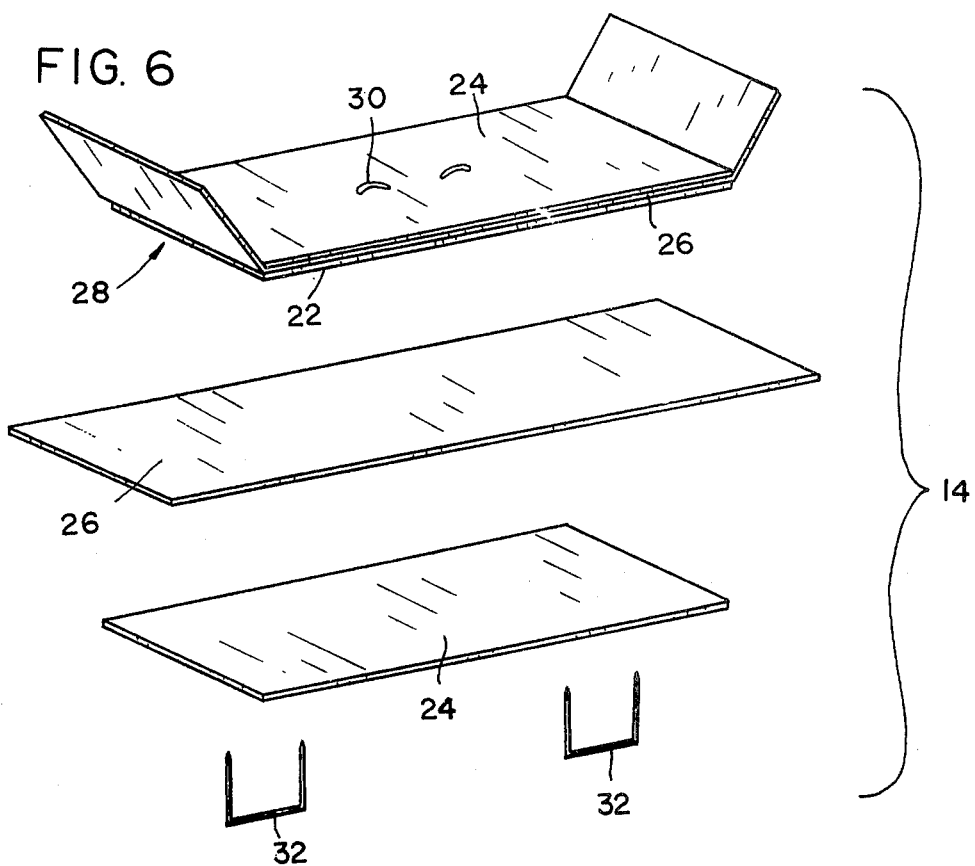
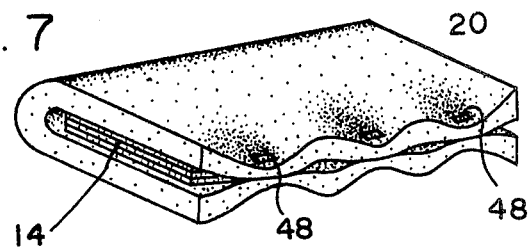

SELF-CONTAINED WARMING PAD

BACKGROUND OF THE INVENTION

This invention relates to a pad for providing topical heat and in particular to a self-contained warming pad for conveniently providing a source of heat which can be used in situations where heat sources are normally inaccessible.

The prior art includes disclosures of heating pads of various types for use in a wide variety of applications. A number of such pads are designed for convenient use. For example, certain chemical pads include two exothermically reactive substances separated one from another within a plastic bag or the like. Such a heating pad may be activated by fracturing a separator (an internal container for an actuating liquid) and allowing intermixture of chemicals to provide heat. Other known heating pads utilize an electrochemical element of the type described by Kober in U.S. Pat. No. 3,774,589. These pads, which may be activated by the addition of water or an electrolyte solution from outside the pad, have been successfully utilized commercially. These and other known heating pads have substantial disadvantages in certain applications.

The prior art heating pads including the self-contained heating pads (that is, those containing all necessary energy and/or material for activation) do not provide a convenient form of heat for specific applications such as the warming of hands during recreational or work activities in cold environments. Chemical heating pads are often rather difficult to activate and are normally too heavy for convenient portability, and too bulky and/or cumbersome for convenient use in such applications.

Other specific problems relate to difficulty in providing a controlled high temperature for extended durations in the activated heating elements for safe and effective topical use on human skin. In some pads peak temperatures are not controlled, giving rise to the risk of burns. In other pads, the temperature curve falls off rapidly such that effective heat is available only briefly.

Known electrochemical heating pads are not self-contained and require special activating procedures which are not viable in many applications. Thus, accessibility of an activating fluid poses a specific problem for the use of such pads as handwarmers and the like. Furthermore, adding activating fluid to an electrochemical heating element gives rise to concomitant problems relating to the amount and/or concentration of activating fluid used. These problems can include overheating, insufficient activation, wetting and the like.

The heat-producing potential of various pads, including certain pads using electrochemical heating elements, is often limited by the inaccessibility of air to the heat-producing site of such pads during operation. However, measures taken to allow a supply of air at the heat-producing site tend to open the pad cover, thus exposing to the outside or allowing the leakage of liquids. In other words, to optimize the heat-producing ability of a pad the human user might have to risk exposure of his skin to these liquids, with a possible attendant feeling of discomfort.

In summary, this invention addresses the need for a warming pad which is lightweight, limited in size and bulk, conveniently activated, safe is use, self-contained, and capable of providing substantial surface temperatures and delivering substantial heat for sustained periods, that is, a heating pad for convenient, reliable topical use in specific applications such as the warming of hands in recreational or work activities in cold environments.

BRIEF SUMMARY OF THE INVENTION

The present invention overcomes each of the aforementioned problems or shortcomings by providing a self-contained warming pad which is light in weight, small in size, conveniently activated, safe during use and capable of producing sustained surface temperatures and delivering substantial amounts of beneficial heat for topical use. The warming pad disclosed in the present invention includes a heating element, preferably an electrochemical heating element, a dose of activating liquid beside the element and within a frangible container, and a substantially liquid-impervious cover for the element and container which defines at least one tortuous air passage therethrough to allow proper activation and sustained production of heat while at the same time preventing liquid in the pad from exiting the pad.

The cover for the heating element and container of activating liquid preferably includes a layer of thermal insulation. Such a cover would not only prevent permeation by the liquids inside but would serve to protect the skin of a user from the intense heat of the heating element. The tortuous air passage through the cover is preferably in the form of a peripheral annular breathing passage about the edge of the pad. Such passage may be formed by two sheets of heat sealable material which form the cover. The sheets are sealed together by inner and outer annular peripheral seals, the inner seal extending about the element and the container to form a central enclosure for them, and the outer seal extending about and spaced from the inner seal to form a peripheral air passage between the seals. Two peripherally spaced openings in the peripheral air passage complete a preferred tortuous air passage through the cover. One of the openings is defined by the inner seal to allow fluid communication between the central enclosure and the peripheral passage, and the other opening is defined by the cover to allow fluid communication between the atmosphere and the peripheral passage.

A porous resilient mass may be placed within the pad to provide a breathing capacity. As the pad is squeezed, the porous mass is squeezed to effect a breathing action through the tortuous air passage.

Another specific feature of this invention is the use of a frangible container and specifically a container made of a meltable substance chosen to have a melting point which can control the upper temperatures of the pad. For example, if the heating element itself is designed to achieve upper temperatures within the range of 160°-170° F, but a temperature of 160° F is considered an optimal maximum for the pad, the material forming the frangible container for activating liquid could be a wax having a melting point of about 160° F. Then, as the pad is activated and its temperature increases, much of the heat which would otherwise generate surface tempertures in excess of 160° F would be absorbed by the meltable substance (the wax) as its heat of fusion.

It can be seen that in theory a control is thus placed on the upper temperatures of the heating pad. The precise mode of operation of such embodiments is dependent upon a number of factors which can be understood by one skilled in the art to whom this invention has been disclosed. Among these factors are the weight of the heating pad, the types of materials used in its construction, the amount of electrolyte solution utilized, the electrolyte concentration, the uniformity of construction of the pad, uniformity of activation procedures, the amount of meltable substance used, the proximity of the meltable substance to the heating element, and the like.

The controlled dosage of activating liquid provided to the heating element in this invention has the advantage of providing substantial performance reproducibility from pad to pad. With this invention, the amount of activating fluid may be controlled to provide an optimum dose to achieve desired heating without risking overheating, insufficient activation, pad leakage and the like. This is an important factor for achieving product efficacy and product safety.

The heating element used in this invention is preferably an electrochemical element of the type described by Frederick P. Kober in U.S. Pat. No. 3,774,589, and, most preferably, a complex electrochemical element having two cathode layers and one anode layer in a sandwich-like structure as described by Frederick P. Kober in a concurrently filed co-pending application entitled COMPLEX ELECTROCHEMICAL HEATING ELEMENT. U.S. Pat. No. 3,774,589 is incorporated here by reference for its disclosure on construction and operation of electrochemical heating elements.

OBJECTS OF THE INVENTION

One object of this invention is to provide a warming pad which is convenient for use in specific topical applications such as hand warming in a cold environment.

Another object of this invention is to provide a warming pad which is light in weight.

Another object of this invention is to provide a warming pad having the aforementioned advantages while being small in size for easy portability and convenient use.

Yet another object of this invention is to provide a self-contained warming pad which is conveniently activated.

Another object of this invention is to provide a warming pad having improved safety during use.

Still another object of this invention is to provide a self-contained warming pad which is capable of producing sustained and controlled surface temperatures and delivering substantial amounts of beneficial heat for topical use.

Another object of this invention is to provide a warming pad having improved reproducibility in heat-generating characteristics.

These and other important objects of the invention will be apparent from the following description of preferred embodiments and the discussion relating thereto.

BRIEF DESCRIPTION OF THE DRAWINGS

FIG. 1 is a perspective view of a self-contained warming pad according to this invention.

FIG. 2 is a top plan view of the device of FIG. 1.

FIG. 3 is an enlarged side sectional view as indicated by Section 3-3 in FIG. 2.

FIG. 4 is a top plan view of the device of this invention with the cover removed.

FIG. 5 is an enlarged perspective view of a preferred heating element which may be used in the warming pad of this invention.

FIG. 6 is a partially exploded perspective view of the device of FIG. 5.

FIG. 7 is a perspective view of the device of this invention with the cover and frangible container removed.

DETAILED DESCRIPTION OF PREFERRED EMBODIMENTS

Throughout the drawings like numerals are used to describe like parts in the illustrated embodiments of this invention.

FIGS. 1 and 2 are perspective and top plan views of a preferred warming pad 10 of this invention showing cover 12 enclosing the internal parts of the device. FIG. 3 is a side sectional view which best illustrates the various parts of the device of this invention, including heating element 14, a dose 16 of activating liquid adjacent element 14 but separated therefrom, a frangible container 18 for liquid dose 16 and a substantially liquid impervious cover 12 which encloses heating element 14 and container 18. Surrounding element 14 is a foam wraparound 20, which is a porous, resilient mass.

A preferred heating element 14 is shown best in FIGS. 5 and 6. Heating element 14 is an electrochemical element having several layers including an anode layer 22, two cathode layers 24 and two separator layers 26. Anode layer 22, cathode layers 24 and separator layers 26 may be chosen of materials described in U.S. Pat. No. 3,774,589.

Anode layer 22 is made of an electrochemically active, electrically conductive, oxidizable material such as zinc, aluminum, magnesium, cadmium, lead, or alloys thereof. Anodes of aluminum and magnesium or their most common alloys are preferred because of their high inherent energy content and lack of concern for toxicity. Anode layer 22 preferably takes the form of a thin metallic sheet or foil, or a layer of powder, chips, granules or turnings pressed or rolled into a suitable conductive body.

Cathode layers 24 include an electrochemically active, nonmetallic, reducible substance which is conductive. Cathode layers 24 need not be formed of a reducible substance, but may be made to provide an electrochemically active surface upon which another material, for example, oxygen on an activated carbon-air electrode, is reduced. Cathode layer 24 may be formed of a wide variety of substances such as manganese dioxide, metadinitrobenzene, silver chloride, silver oxide, copper chloride and air depolarized cathode structures of the carbon and metal type.

Separator layers 26 are formed of a non-conductive, porous, absorbent material such as cotton, felt, or bibulous papers, which enable ions of an electrolyte to freely pass between the anode layer and the cathode layers. The separator material is sized to absorb and hold a sufficient amount of electrolyte solution to sustain the high rate electrochemical reaction to completion.

As illustrated best by FIG. 6, the electrochemical heating element 14 may be constructed by first making a subassembly 28 having anode layer 22 and one each of the separator layers 26 and cathode layers 24. Subassembly 28 is held together by a fastening staple 30 which is an electrically conductive connector means extending through the three layers. Subassembly 28 is in turn assembled with the remaining separator layer 26 and the remaining cathode layer 24 by means of fastening staples 32 which extend through all five layers, as shown in FIG. 5.

As shown in FIGS. 5 and 6, electrically conductive connector means 30 and 32 extend through the five layered element, electrically connecting the anode layer 22 and the cathode layers 24 through the separator layers 26. Connectors 30 and 32 are sized to support the short circuiting current produced when the electrochemical heating element is activated. Connectors 30 and 32, which are integrally contained as part of the element, serve a dual purpose: (1) holding the overall heater sandwich structure together — keeping the individual layers in proper juxtaposition to one another, and (2) providing an internal short-circuiting means between the anode and cathode structures. Consequently, the fastening means must be mechanically strong while at the same time being electrically conductive. The fastening means may be selected from metal rivets, metal wire or staples, conductive carbon thread or similar materials. From the standpoint of heater performance, economics and ease of production, metal wire or staples are preferred.

When activating liquid 16 is within separator layers 26, staples 30 and 32 conduct an electric heating current between anode layer 22 and cathode layers 26. When heating element 14 is an electrochemical element, the dose of activating liquid 16 is preferably an electrolyte formed of an ionically conductive medium. The electrolyte may be an aqueous salt solution such as table salt (NaCl), or may be selected from a host of many other well known electrolyte materials. For those warming pads in which extremely high heat output is essential, highly acid or alkaline electrolytes can be used to great advantage. For example, water can be used in combination with a lithium metal anode, the electrolyte being lithium hydroxide, which is produced spontaneously upon contact of the water with the lithium. However, for the wide range of more common warming pad applications, electrolytes consisting of an aqueous solution of sodium or magnesium chloride are preferred.

The electrolyte solution is introduced into separator layers 26 when activating fluid 16 from frangible container 18 is introduced to separator layers 26 upon intentional fracturing of container 18. As already stated, activating liquid 16 is preferably an electrolyte solution. Alternatively, the dry electrolytic salt can be intermixed or dispersed within the cathode or anode materials or placed within separator layers 26. In such cases, activating fluid 16 would preferably be water which would dissolve the salt to form an electrolyte within the separator material. Obviously, combinations of these ideas can also be used to good advantage. The choice of a precise method for introducing an electrolyte into separator layers 26 is governed by requirements for speed in initiation of the reaction. It is highly preferred, however, to use an activating liquid which is an electrolyte solution; in such cases the electrochemical action is initiated substantially instantaneously.

Frangible container 18, which contains activating fluid 16, may be made of glass, wax, plastics, and a variety of other materials. It is essential it be constructed to allow ready breakage by a user to activate the pad. Such breakage occurs upon the application of bending or crushing pressure on container 18, by a user, through cover 12 of the pad.

It is highly preferred that frangible container 18 be made of a meltable substance having a melting point such that the heat of fusion of the material can control upper temperatures of the warming pad when heating element 14 is activated. Examples of suitable meltable material for use in a warming pad of a type which could be used as a handwarmer are parrafin waxes, microwaxes, polyethylene waxes, and blends thereof. Other acceptable waxes and other meltable materials would be apparent to those skilled in the art who have received disclosure of this invention. The primary properties to be considered are the breaking characteristics and the melting point.

Preferred breaking characteristics are such that the container would shatter when moderate bending or crushing pressure is applied through cover 12. Melting points are chosen with consideration to the desired upper temperatures. It should be noted that a melting point which is too low would cause complete melting of the container which could interfere with operation of the heating element and rob the element of effective heat output. On the other hand, a melting point which is well above and maximum temperatures of the heating element would prevent the heat of fusion from being a useful control. Warming pads for topical use on humans should have a temperature within the range of about 110° to 190° F, and preferably within the range of about 140° to 170° F. Melting points of a container material can be selected accordingly, bearing in mind, of course, the heat-generating characteristics of the heating element itself.

One advantage of certain wax materials is ease of breaking by bending or crushing through cover 12, which encloses container 18. A related advantage is the safety which is provided in that such waxes do not form sharp edges and points which could protrude through cover 12 and cut the skin of a user.

Foam wraparound 20, shown best in FIGS. 3, 4, and 7, preferably has surface characteristics such that it repels the electrolyte solution or other activating liquid 16, enabling activating liquid 16 to be absorbed readily into separator layers 26. If an aqueous electrolyte is used as activating liquid 16, foam wraparound 20 preferably would be hydrophobic. Given suitable hydrophobicity, the foam may have open pores; closed-pore foams, however, are acceptable. A highly preferred material for foam wraparound 20 is a polyether foam known as Foam P-65 available from Stephenson & Lawyer, Inc., of Grand Rapids, Mich. Other acceptable foams include polyethers, polyethylenes, and polyurethanes. Acceptable foams would be apparent to those skilled in the art who have received disclosure of this invention.

The primary function of foam wraparound 20 is to provide breathing capacity within warming pad 10 as will be explained hereafter. The porous resilient mass which provides such breathing capacity need not be in the form of a wraparound as is shown in FIGS. 3, 4, and 7. A porous resilient mass of essentially any shape may be placed anywhere adjacent heating element 14 where it may be flexed through cover 12 of warming pad 10 to provide the aforementioned breathing. Foam wraparound 20, as shown best in FIGS. 3, 4 and 7, may be constructed by spot heat sealing of the adjacent opposite edges. Spot seals 48 are spaced along such edge in a manner allowing ample access of activating fluid 16 to heating element 14 when container 18 is broken for activation.

Cover 12 of warming pad 10 has defined therein a tortuous air passage which provides air to heating element 14 to sustain and/or increase the heat-producing reaction. The tortuous air passage through cover 12 cooperates with foam wraparound 20. As foam mass 20 is flexed, air passes through the tortuous air passage.

As shown best in FIGS. 1 - 3, cover 12 is formed of two sheets 34 of sealable, preferably heat sealable, material. Sheets 34 are preferably sealed together by heat sealing techniques at an inner peripheral seal 36 and an outer peripheral seal 38. Inner seal 36 extends about heating element 14 and frangible container 18 enclosing them within a central enclosure 40. Outer seal 38 extends about and is spaced from inner seal 36. A peripheral air passage 42 is formed between seals 36 and 38. Other sealing means, such as adhesives, can be used as an alternative to heat sealing.

Peripheral air passage 42 is the principal part of the aforementioned tortuous air passage through which the warming pad breathes. Inner seal 36 defines a first opening 44 which is, in effect, an incomplete portion of inner seal 36. First opening 44 permits fluid passage between central enclosure 40 and peripheral air passage 42. Cover 12 defines a second opening 46 in peripheral passage 42 which allows fluid communication between the atmosphere and peripheral air passage 42. First opening 44 and second opening 46 are peripherally spaced, and, preferably, on opposite edges of warming pad 10, as shown in FIGS. 1 and 2, to minimize the possibility of leakage of activating fluid 16 from the pad during activation, while still allowing substantial breathing of the pad.

Cover 12 may be made to be substantially liquid-impervious to eliminate contact of activating fluid 16 with the skin of a user. A wide variety of materials are acceptable for cover 12, including plastics such as polyethylenes, polypropylenes and polyurethanes, and natural materials such as rubber. Cover 12 preferably has thermal insulating properties. Such properties may be provided using cover materials made of foam. Such foam covers may be made of closed-pore foams which would be both liquid-impervious and thermally insulating. Laminated materials are also acceptable. A highly preferred cover material is a DuPont laminate having a one-sixteenth inch layer of DuPont Microfoam and a 0.002 inch layer of DuPont Surlyn. Various acceptable cover materials would be apparent to those skilled in the art who have received a disclosure of this invention.

While in the foregoing specification, this invention has been described in relation to certain preferred embodiments, and many details have been set forth for purpose of illustration, it will be apparent to those skilled in the art that the invention is susceptible to additional embodiments and that certain of the details described herein can be varied considerably without departing from the basic principles of the invention.

We claim:
1. A self-contained warming pad comprising:
   a heating element;
   a dose of activating liquid adjacent to said element and separate therefrom;
   a frangible container containing said liquid; and
   a substantially liquid-impervious covering layer means to enclose said element and said container, said layer means defining at least one tortuous air passage therethrough, whereby said layer means serves both to promote sustained production of heat and to prevent liquid from exiting the pad.
2. The pad of claim 1 wherein said frangible container is made of a meltable substance having a melting point such that its heat of fusion can control upper temperatures when activated.
3. The pad of claim 1 wherein said cover comprises a layer of thermal insulation.
4. The pad of claim 2 wherein said cover includes a layer of thermal insulation.
5. The pad of claim 1 wherein:
   said heating element comprises an electrochemical element having an anode layer of an electrochemically active, electrically-conductive, oxidizable material, a cathode layer of an electrochemically active, nonmetallic, reducible material, and a separator layer of porous, absorbent material between said anode and cathode layers, and electrically-conductive connector means extending through said anode, separator and cathode layers to conduct an electric heating current between the anode and cathode layers; and
   said activating liquid comprises an electrolyte solution.
6. The pad of claim 5 wherein said frangible container is made of a meltable substance having a melting point such that its heat of fusion can control upper temperatures when activated.
7. The pad of claim 5 wherein said cover comprises a layer of thermal insulation.
8. The pad of claim 5 wherein said tortuous air passage comprises a peripheral air passage formed near the edge of said cover.
9. The pad of claim 8 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.
10. The pad of claim 5 further including a porous, resilient mass around said heating element and within said cover whereby to provide a breathing capacity inside said cover.
11. The pad of claim 6 wherein said cover includes a layer of thermal insulation.
12. The pad of claim 6 wherein said tortuous air passage comprises a peripheral air passage formed near the edge of said cover.
13. The pad of claim 12 wherein said cover is formed of two sheets of heat sealable material, said sheets sealed together by inner and outer annular peripheral seals, said inner seal extending about the element and the container for form a central enclosure therefor, said outer seal extending about and spaced from the inner seal to form said peripheral air passage between the seals, said inner seal defining a first opening in the peripheral passage, to the central enclosure, and said cover defining a second opening of the peripheral passage, to the atmosphere, said first and second openings being peripherally spaced.
14. The pad of claim 6 further including a porous, resilient mass around said heating element and within said cover whereby to provide a breathing capacity inside said cover.
15. The pad of claim 14 wherein said tortuous air passage comprises a peripheral air passage formed near the edge of said cover.
16. The pad of claim 15 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.

17. The pad of claim 16 wherein said cover comprises a layer of thermal insulation.

18. The pad of claim 5 wherein said electrochemical heating element comprises a five-layered sandwich-like structure including, in order, said cathode layer, said separator layer, said anode layer, a second separator layer and a second cathode layer.

19. The pad of claim 18 wherein said frangible container is made of a meltable substance having a melting point such that its heat of fusion can control upper temperatures when activated.

20. The pad of claim 18 wherein said cover comprises a layer of thermal insulation.

21. The pad of claim 18 wherein said tortuous air passage comprises a peripheral air passage formed near the edge of said cover.

22. The pad of claim 21 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.

23. The pad of claim 18 further including a porous, resilient mass around said heating element and within said cover whereby to provide a breathing capacity inside said cover.

24. The pad of claim 19 wherein said cover includes a layer of thermal insulation.

25. The pad of claim 19 wherein said tortuous air passage comprises a peripheral air passage formed near the edge of said cover.

26. The pad of claim 25 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening of the peripheral passage, to the atmosphere, said first and second openings being peripherally spaced.

27. The pad of claim 19 further including a porous, resilient mass around said heating element and within said cover whereby to provide a breathing capacity inside said cover.

28. The pad of claim 27 wherein said tortuous air passage comprises a peripheral air passage formed near the edge of said cover.

29. The pad of claim 28 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.

30. The pad of claim 29 wherein saidcover comprises a layer of thermal insulation.

31. A self-contained warming pad comprising:
a heating element;
a dose of activating liquid adjacent to said element and separate therefrom;
a frangible container containing said liquid; and
a substantially liquid-impervious cover enclosing said element and said container and defining at least one tortuous air passage therethrough, said passage comprising a peripheral air passage formed near the edge of said cover.

32. The pad of claim 31 wherein said cover is formed of two sheets of sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.

33. A self-contained warming pad comprising:
a heating element;
a dose of activating liquid adjacent to said element and separate therefrom;
a frangible container containing said liquid;
a substantially liquid-impervious cover enclosing said element and said container and defining at least one tortuous air passage therethrough; and
a porous resilient mass adjacent to said heating element whereby to provide a breathing capacity inside said cover.

34. The pad of claim 33 wherein said porous resilient mass is around said heating element within said cover.

35. A self-contained warming pad comprising:
a heating element;
a dose of activating liquid adjacent to said element and separate therefrom;
a frangible container containing said liquid, said container being made of a meltable substance having a melting point such that its heat of fusion can control pad upper temperatures when activated; and
a substantially liquid-impervious cover enclosing said element and said container and defining at least one tortuous air passage therethrough, said passage comprising a peripheral air passage formed near the edge of said cover.

36. The pad of claim 35 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening of the peripheral passage, to the atmosphere, said first and second openings being peripherally spaced.

37. A self-contained warming pad comprising:
a heating element;
a dose of activating liquid adjacent to said element and separate therefrom;
a frangible container containing said liquid, said container being made of a meltable substance having a melting point such that its heat of fusion can control pad upper temperatures when activated;
a substantially liquid-impervious cover enclosing said element and said container and defining at least one tortuous air passage therethrough; and
a porous resilient mass adjacent to said heating element whereby to provide a breathing capacity inside said cover.

38. The pad of claim 37 wherein said porous resilient mass is around said heating element within said cover.

39. The pad of claim 38 wherein said tortuous air passage comprises a peripheral air passage formed near the edge of said cover.

40. The pad of claim 34 wherein said cover is formed of two sheets of heat sealable material, said sheets sealed together by inner and outer annular peripheral seals, said inner seal extending about the element and the container to form a central enclosure therefor, said outer seal extending about and spaced from the inner seal to form said peripheral air passage between the seals, said inner seal defining a first opening in the peripheral passage, to the central enclosure, and said cover defining a second opening in the peripheral passage, to the atmosphere, said first and second openings being peripherally spaced.

41. The pad of claim 40 wherein said cover comprises a layer of thermal insulation.

* * * * *

UNITED STATES PATENT OFFICE
CERTIFICATE OF CORRECTION

Patent No. 4,095,583          Dated June 20, 1978

Inventor(s) Russell H. Peterson, Edmund A. Weaver, and Frederick P. Kober

It is certified that error appears in the above-identified patent and that said Letters Patent are hereby corrected as shown below:

Column 6, line 16 - Delete "and" and insert "the".

Column 12, line 4 - Delete "34" and insert "39".

Signed and Sealed this

Sixteenth Day of January 1979

[SEAL]

Attest:

RUTH C. MASON
*Attesting Officer*

DONALD W. BANNER
*Commissioner of Patents and Trademarks*